US00PP37000P2

(12) United States Plant Patent
Lim

(10) Patent No.: US PP37,000 P2
(45) Date of Patent: Oct. 7, 2025

(54) ***HIBISCUS* PLANT NAMED 'ALTobiscus'**

(50) Latin Name: *Hibiscus rosa-sinensis*
Varietal Denomination: ALTobiscus

(71) Applicant: Altman Specialty Plants llc, Vista, CA (US)

(72) Inventor: Peter Lim, Escondido, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/022,390

(22) Filed: Jan. 15, 2025

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — Cassandra Bright

(57) ABSTRACT

A new and distinct cultivar of *Hibiscus* plant named 'ALTobiscus' is disclosed, characterized by multicolored flower with a dark red center radiating into a large bright pink ring and a thick orange margin. Flowers have thick, ruffled petals. Flowers are 16 to 20 centimeters in diameter. The new variety is a *Hibiscus,* typically produced as an ornamental plant.

1 Drawing Sheet

Latin name of the genus and species: *Hibiscus rosa-sinensis.*

Variety denomination: 'ALTobiscus'.

BACKGROUND OF THE INVENTION

The new *Hibiscus* cultivar is a product of a planned breeding program conducted by the inventor, Peter Lim. The objective of the breeding program was to produce vigorous *Hibiscus rosa-sinensis* cultivars for commercial ornamental applications. The cross resulting in this new variety was made Aug. 22, 2016.

The seed parent is the unpatented *Hibiscus rosa-sinensis* 'Love Story'. The pollen parent is the unpatented variety *Hibiscus rosa-sinensis* 'Faith'. The new variety was identified and selected as a potentially interesting selection in August of 2019. Selection was made at a commercial nursery in Vista, California.

Asexual reproduction of the new cultivar 'ALTobiscus' was first performed in August of 2019 in Vista, California, by vegetative cuttings. Subsequent propagation has shown that the unique features of this cultivar are stable and reproduced true to type in successive generations.

SUMMARY OF THE INVENTION

The cultivar 'ALTobiscus' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTobiscus'. These characteristics in combination distinguish 'ALTobiscus' as a new and distinct *Hibiscus* cultivar:

1. Multicolored flower with a dark red center radiating into a large bright pink ring and a thick orange margin.
2. Thick and ruffled petals.
3. Large flowers with diameters from 16 to 20 cm.

PARENT COMPARISONS

Plants of the new cultivar 'ALTobiscus' are similar to the seed parent 'Love Story', in most horticultural characteristics. However, characteristics of the new cultivar differ in the following:

1. Flowers of the new cultivar have a dark red center radiating into a large bright pink ring and a thick orange margin; flowers of the seed parent are red with white feathering.
2. Plants of the new cultivar are more compact than plants of the seed parent.

Plants of the new cultivar 'ALTobiscus' are similar to the pollen parent in most horticultural characteristics. However, characteristics of the new cultivar differ in the following:

1. The new cultivar has multicolored flower with a dark red center radiating into a large bright pink ring and a thick orange margin; the pollen parent has an dark orange flower with a small red center.

COMMERCIAL COMPARISON

Plants of 'ALTobiscus' are similar in some horticultural characteristics to the variety *Hibiscus* 'DUP-IDP', U.S. Plant Pat. No. 27,086. The new variety, however, differs in the following:

1. Flowers of 'ALTobiscus' have a less ruffled margin than flowers of 'DUP-IDP'.
2. Plants of 'ALTobiscus' are smaller than plants of 'DUP-IDP' by about 30%.
3. Flowers of the new cultivar have a dark red center radiating into a large bright pink ring and a thick orange margin; flowers of 'DUP-IDP' have a bright purple center radiating into salmon orange.

Plants of 'ALTobiscus' are similar in some horticultural characteristics to the variety *Hibiscus* 'The Path', unpatented. The new variety, however, differs in the following:

1. Foliage of 'ALTobiscus' is lighter green than foliage of 'The Path'.
2. Plants of 'ALTobiscus' are smaller than plants of 'The Path' by about 80%.
3. Flowers of the new cultivar have a dark red center radiating into a large bright pink ring and a thick orange margin; flowers of 'The Path' are yellow with a bright pink center.

BRIEF DESCRIPTION OF THE PHOTOGRAPH

The accompanying photograph illustrates in full color typical flowers of 'ALTobiscus' from a plant grown outdoors at a commercial nursery in Vista, California.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'ALTobiscus' plant. This plant was grown a commercial nursery in Vista, California. The growing temperature ranged from about 7° C. to 30° C. during the day and from about 5° C. to 12° C. during the night. No artificial light, photoperiodic treatments were given to the plants. Measurements and numerical values represent averages of typical plant types.

Botanical classification: *Hibiscus rosa-sinensis* 'ALTobiscus'.

PROPAGATION

Typical method: Hardwood stem cuttings.

Root description: Roots are fine, fibrous and well branched. Tan/brown in color, not effectively measured with a color chart.

PLANT

Plant type: Tender, woody flowering shrub.

Age of plant described: Approximately 1.5 years old.

Growth habit: Compact.

Height: 50 cm.

Plant spread: 45 cm.

Branching characteristics: 2 to 4 breaks from a pinch, occurring at an average 45° angle.

Length of primary lateral branches: 20 to 60 cm.

Quantity of lateral branches: Each primary lateral branch has 3 to 6 laterals.

Characteristics of primary lateral branches:

*Diameter.*—Average range 15 to 20 mm.

*Color.*—New growth RHS Green 143B. Mature growth RHS Greyed-Green 197A, striated Grey-Brown N199A.

*Texture.*—New growth very sparsely hirsute, older growth striated.

Internode length: Average 3 cm.

FOLIAGE

Leaf:

*Arrangement.*—Alternate.

*Quantity.*—Average 10 to 16 per branch.

*Leaf internode.*—1.8 to 3 cm.

*Average length.*—7 to 8 cm, excluding petiole.

*Average width.*—7 to 8 cm.

*Shape of blade.*—Cordate.

*Apex.*—Acute.

*Base.*—Cordate.

*Margin.*—Entire or irregularly and shallowly crenate.

*Aspect.*—Moderately undulating.

*Texture of top surface.*—Glabrous.

*Texture of bottom surface.*—Sparse and very short hirsute.

*Color.*—Young foliage upper side: RHS Green 137C. Young foliage under side: RHS Green 143A. Mature foliage upper side: RHS Green 137A. Mature foliage under side: RHS Green 137B.

*Venation.*—Type: Pinnate. Venation color, upper side: RHS Green 137B. Venation color, under side: RHS Green 143B.

*Petiole.*—Length: 1.8 to 3.8 cm. Diameter: 4 to 5 mm. Color: Near RHS Green 143B. Texture: Very short hirsute.

*Leaf stipule.*—Not observed.

FLOWER

Natural flowering season: Late Spring through Fall.

Flower type and habit: Solitary, rotate.

*Single, double, multiplex.*—Single.

*Petals overlapping.*—Strongly overlapping.

Quantity of flowers: A plant of about 2 years old has approximately 30 open flowers at one time during Summer.

*Rate of flower opening.*—4 to 6 days from bud to fully opened flower.

*Flower longevity on plant.*—1 to 2 days.

Persistent or self-cleaning: Self-cleaning.

Bud:

*Shape.*—Ovate.

*Length.*—4 cm.

*Diameter.*—2.2 cm.

*Color.*—RHS Yellow 2C.

Flower size:

*Diameter.*—16 to 20 cm.

*Depth.*—7.5 cm 12 cm to end of protruding stamen.

Petals:

*Quantity.*—5.

*Arrangement.*—Whorled, strongly overlapping.

*Length.*—9 cm.

*Width.*—10 cm.

*Shape*: Slightly asymmetrical broad spatulate.

*Apex.*—Obtuse rounded with irregular, shallow crenations.

*Base.*—Attenuate.

*Margin.*—Entire. Strong undulation.

*Texture.*—Glabrous all surfaces. Strongly rugose top and bottom.

*Color.*—When opening, upper surface: Large basal blotch (forming flower eye) Red N45A changing to Red 45C and finally feathering out to 52A at outermost eye. Thick margin near Orange-Yellow 21A. When opening, lower surface: RHS Orange-Yellow 21A. streaked Red N45C and N45D. Thick basal White N155D. Fully opened, upper surface: Large basal blotch (forming flower eye) Red N45A changing to Red 45C and finally feathering out to 52A at outermost eye. Thick margin near Orange-Yellow 21B. Fully opened, lower surface: RHS Orange-Yellow 21A. streaked Red N45C and N45D. Thick basal White N155D. Ratio of basal blotch/eye to petal size: Overall 80% of petal blade is blotched. 70% solidly blotched, 10% feathered blotch. Feathering: Minimal.

Sepals:
- *Quantity.*—5.
- *Length.*—3.4 cm.
- *Width.*—1.4 cm.
- *Shape.*—Deltate.
- *Margin.*—Entire.
- *Apex.*—Acute.
- *Base.*—Fused.
- *Color.*—Upper surface: RHS Yellow-Green 145A, base 145C. Lower surface: RHS Yellow-Green 144C, base 144D.
- *Texture.*—Upper surface: Softly pubescent. Lower surface: Very short hirsute.

Epicalyx:
- *Quantity of bracts.*—6.
- *Bract length.*—1.2 cm to 1.4 cm.
- *Bract width.*—3 to 5 mm.
- *Bract shape.*—Straplike.
- *Bract margin.*—Entire.
- *Color.*—Upper surface: RHS Green 143A. Lower surface: Near RHS Green 137C.
- *Texture.*—Upper surface glabrous, lower surface non-pubescent rough.

Peduncles:
- *Length.*—4 to 6 cm.
- *Diameter.*—4 to 5 mm.
- *Angle.*—Approximately 45° to the lateral branch.
- *Strength.*—Strong.
- *Texture.*—Sparsely hirsute.
- *Color.*—RHS Green 143A.

Fragrance: Faint grassy scent.

REPRODUCTIVE ORGANS

Stamens:
- *Number.*—About 40 to 50.
- *Filament length.*—7 mm.
- *Filament color.*—Near Yellow 13D.

Anthers:
- *Shape.*—Irregular sphere.
- *Length.*—About 3 mm.
- *Color.*—Near RHS Yellow-Orange 18A.
- *Pollen color.*—Near RHS Yellow-Orange 18B.
- *Pollen amount.*—Scant.

Pistil:
- *Number.*—1.
- *Length.*—10 cm.
- *Style.*—Length: 7.2 cm. Color: Lower section near Red 46A, flushed Red-Purple N66B. Uppermost 1/3 White N155C.
- *Stigma.*—Shape: Peltate. Color: Near RHS Orange N25C.
- *Ovary color.*—Near RHS Yellow 4D.
- *Ovary length.*—1.2 cm.
- *Ovary width.*—7 mm.

OTHER CHARACTERISTICS

Seeds: Not observed.

Disease/pest resistance: Neither resistance nor susceptibility to normal diseases and pests of *Hibiscus rosa-sinensis* have been observed.

Temperature tolerance: USDA Zones 8 through 11.

What is claimed is:

1. A new and distinct cultivar of *Hibiscus* plant named 'ALTobiscus' as herein illustrated and described.

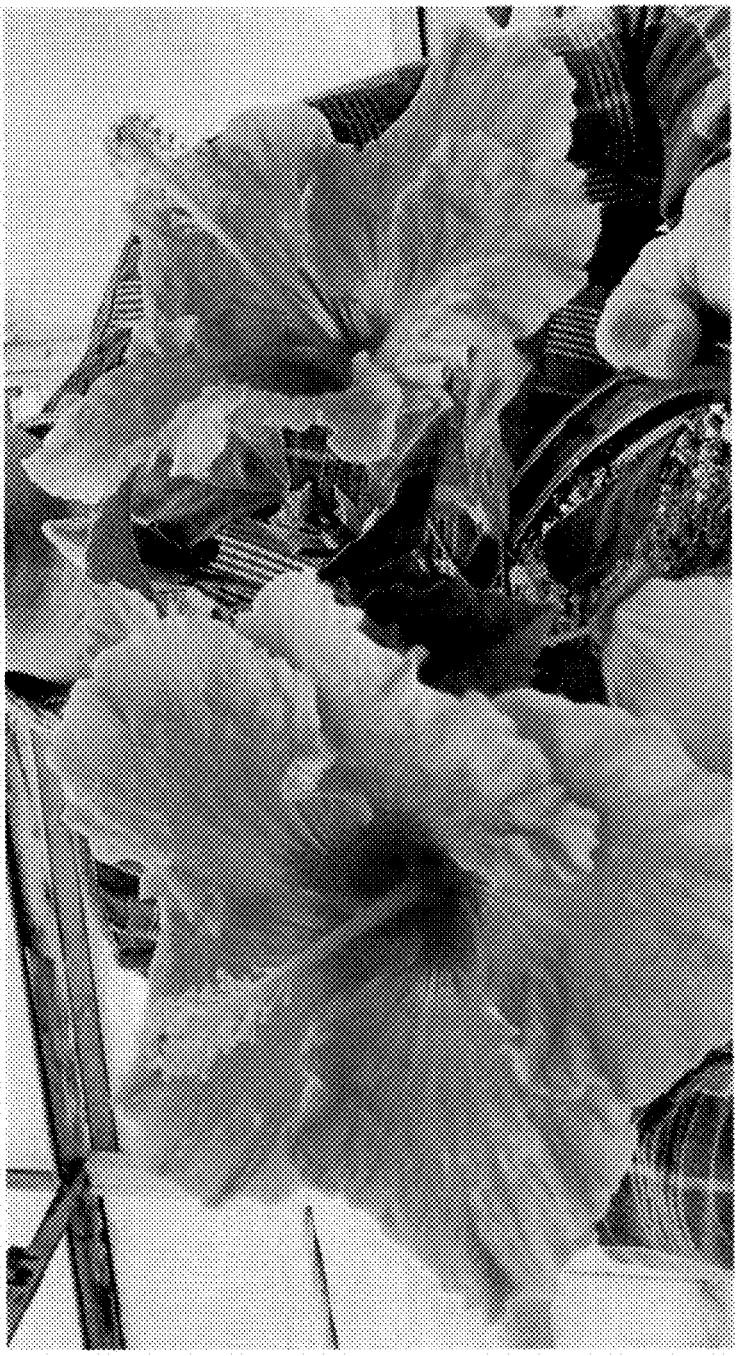

* * * * *